United States Patent [19]

Jones

[11] 4,105,660

[45] Aug. 8, 1978

[54] PREPARATION OF 3β-HYDROXY-27-NORCHOLEST-5,7-DIEN-25-ONE

[75] Inventor: Howard Jones, Holmdel, N.J.

[73] Assignee: Merck & Co., Inc., Rahway, N.J.

[21] Appl. No.: 811,403

[22] Filed: Jun. 29, 1977

[51] Int. Cl.² .......................... C07J 9/00; C07J 21/00
[52] U.S. Cl. ......................... 260/239.55 C; 260/397.2
[58] Field of Search ..................... 260/397.2, 239.55 C

[56] References Cited

PUBLICATIONS

S. J. Halkes et al, Rec. Trav. Chim. Pays–Bas (Recueil), vol. 88, (1969), pp. 1080–1083.

*Primary Examiner*—Elbert L. Roberts
*Attorney, Agent, or Firm*—Rudolph J. Anderson, Jr.; Mario A. Monaco; Martin L. Katz

[57] ABSTRACT

Improved process is described for preparing 3β-hydroxy-27-norcholest-5,7-dien-25-one, a useful intermediate in the synthesis of 25-hydroxyvitamin $D_3$. Novel intermediates and their preparation are disclosed.

2 Claims, No Drawings

PREPARATION OF 3β-HYDROXY-27-NORCHOLEST-5,7-DIEN-25-ONE

The instant invention may be described as residing in the concept of a new and useful process for preparing 3β-hydroxy-27-norcholest-5-7-dien-25-one; to novel intermediates obtained therein; and to the process for preparing such intermediates. The 3β-hydroxy-27-norcholest-5,7-diene-25-one prepared by the novel process of the instant invention is readily converted by techniques already well-known in the art into 25-hydroxyvitamin $D_3$ which is a useful therapeutic agent in antirachitic applications (see Halkes et al., Investigations on Sterols. XXXV-Synthesis of 25-Hydroxycholecalciferol, Rec. Trav. Chim. Pays-Bas (RECUEIL), 88, 1080–1083, 1969).

The instant invention is based upon applicant's discovery that 3β-hydroxy-27-norcholest-5-7-dien-25-one prepared in accordance with the instant invention has the following structural formula:

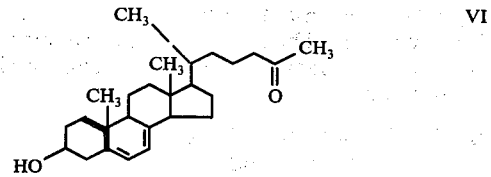

The overall process according to the instant invention is illustrated by the following flow sheet and in the accompanying description of the individual steps therein. The starting material is a known compound, either available commercially or readily prepared by processes already fully described in the literature.

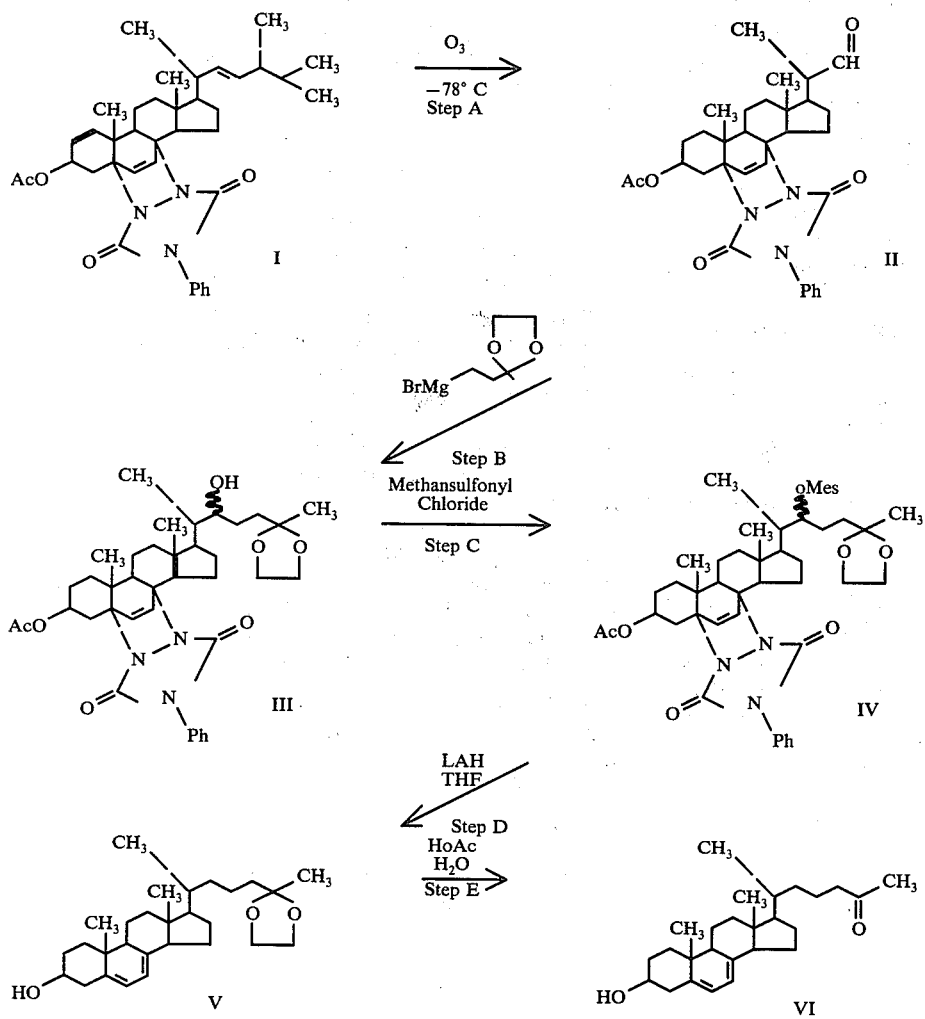

Step A - Ozonazation And Reduction of The 4-phenyl-1, 2, 4-triazoline-3-5dione Adduct of Ergosterol Acetate The ozonazation is readily carried out by treating with ozone the 4-phenyl-1, 2,4-triazoline-3, 5-dione adduct of egosterol acetate (J. Chem. Soc. (C), (1971), 1968-1974), the compound of formula I, in a suitable organic solvent, such as methylene chloride or a mixture of methylene chloride and pyridine or methanol, at low temperature, about −70° to −80° C until the required amount of ozone is taken up. The reaction mixture is allowed to warm to room temperature and the ozonide is then reduced in situ with zinc dust and acetic acid to produce the desired hexanoraldehyde, the compound of formula II. The recovered aldehyde may be purified by chromatography over silica gel eluting with ethyl acetate in benzene.

Step B - Alkylation Of the 4-Phenyl-1,2,4-triazoline-3,5-dione Adduct Of 3β-Actoxycholest-6-en-hexanoraldehyde The alkylation is carried by treating the 4-phenyl-1,2,4-triazoline-3,5-dione adduct of 3β-acetoxycholest-6-en-hexanoraldehyde, the compound of formula II, with the Grignard reagent, 2-(1,3-dioxolane-2-methyl)ethylmagnesium bromide, prepared in situ by adding 2-(1,3-dioxolane-2-methyl)ethyl bromide (Bul. Soc. Chem. France, II, 2575, 1963) in tetrahydrofuran to a mixture of magnesium and iodine in tetrahydrofuran. The hexanoraldehyde in tetrahydrofuran solution is added to the preformed Grignard reagent in the cold, about −20° to −40° C, and the mixture is stirred for 20 to 60 minutes. The reaction is quenched with saturated ammonium chloride and the reaction mixture is extracted with methylene chloride and water. The organic phase is separated, dired and evaporated to dryness. The residue is purified by preparative thin layer chromotography on silica gel plates eluting with ethyl acetate to obtain the ketal of formula III.

Step C - Mesylation Of The 22-Hydroxy Group

The 22-ol from Step B is dissolved in a suitable organic solvent such as pyridine and treated with methenesulfonyl chloride. The reaction conveniently is carried out at room temperature and usually requires from 12 to 24 hours for completion. The reaction mixture is quenched with ice water and the recovered precipitate is employed in the next step without further purification.

Step D - Reductive Elimination Of the Hydroxy Group And the Triazoline Protecting Group The crude mesylate from Step C in a suitable solvent such as tetrahydrofuran is treated with lithium aluminum hydride in small portions at room temperature. After addition of the hydride the reaction mixture is refluxed for 18-36 hours, cooled to 0 to 10° C and quenched with water and ethyl acetate. The reaction mixture is extracted with methylene chloride and the crude product is obtained by evaporation of the methylene chloride phase.

The ketals of formulas III, IV and V are novel compounds and constitute the composition of matter aspect of the instant invention.

Step E - Removal Of the Ketal Group

The ketal of Step D is stirred at room temperature with a mixture of acetic acid and water for 12 to 24 hours and then is extracted with methylene chloride and water. The organic phase is separated, dried, filtered and concentrated to dryness. The product may be purified by preparative thin layer chromatography on 1000 M silica gel plates eluting with 20% ethanol in ethyl acetate. The product so obtained in recrystallized from ethyl acetate to give pure 3β-hydroxy-27-norcholest-5,7-dien-25-one(mp 89°–91° C - not reduced on admixture with an authentic sample -Journal of Labelled Compounds, IX, 339–341, 1973.

As noted above, the 3β-hydroxy-27-norcholest-5,7-dien-25-one prepared in accordance with the process of the instant invention is readily converted by techniques well-known in the art into 25-hydroxyvitamin $D_3$. Thus, as described in the previously cited RECUEIL reference, 3β-hydroxy-27-norcholest-5,7-dien-25-one in dry benzene may be treated with methyl magnesium bromide at about 5° C. The reaction mixture is stirred for 8 – 18 hours and then is worked up by the addition of an aqueous solution of ammonium chloride. The cholest-5,7-diene-3β,25-diol so produced is crystallized from successively tetrahydrofuran-diisopropyl ether and tetrahydrofuran-ethyl acetate.

This diol in dry and peroxide-free tetrahydrofuran is irradiated under nitrogen using a 450 Biosol β lamp for 45 minutes. Addition of dry ether and concentration yields unchanged starting material. Chromotography of the residue over silica gel followed by crystallization from acetone gives 25-hydroxyvitamin $D_3$.

The best mode comtemplated by applicant for carrying out the instant invention is illustrated in the following working examples, no limitation being intended except as set forth in the appended claims.

EXAMPLE 1

3β-Hydroxy-27-norcholest-5-7-dien-25-one

Step A - 4-Phenyl-1,2,4-triazoline-3,5-dione Adduct of 3-62-Acetoxycholest-6-en-hexanoraldehyde Dissolve 6.069 gm of the 4-phenyl-1,2,4-triazoline-3,5-dione adduct of ergosterol acetate in 200 ml of methylene chloride and 2 ml of pyridine and ozonize on a Welsbach ozonizer at about 78° C for 16 minutes at 0.94 m mole/min. (1.5 eq.). Reduce the ozonide in situ with 4.6 gm of zinc dust and 20 ml of acetic acid by stirring for 30 minutes at room temperature. Wash the reaction mixture with two 100 ml portions of 0.1 N hydrochloric acid followed by two 100 ml portions of saturated aqueous soldium bicarbonate solution. Separate the methylene chloride layer, dry over magnesium sulfate, filter and concentrate the filtrate to dryness in vacuo. Chromotograph the residue on 350 gm of silica gel and elute with 20% ethyl acetate in benzene.

Step B - 4-Phenyl-1,2,4-triazoline-3,5-dione Adduct of 22ξ-Hydroxy-27-norcholest-6-ene-3-acetate Ethylene Ketal Place 40 mg of magnesium powder, 5 ml of dry tetrahydrofuran and a crystal of iodine into a 15 ml, 3-neck round-bottom flask. Add 210 mg of 2-(1,3-dioxolane-2-methyl)ethyl bromide dissolved in 2 ml of dry tetrahydrofuran. Stir the mixture at 30°–40° C for one hour while adding 200 mg of excess 2-(1,3-dioxolane-2-methyl)ethyl bromide. Cool the mixture to −30° C and add 500 mg of the 4-phenyl-1,2,4-triazoline-3,5-dione adduct of 3β-acetoxycholest-6-en-hexanoraldehyde from Step A in 5 ml of tetrahydrofuran. Stir the mixture for 30 minutes and add 10 ml of saturated ammonium chloride solution. Extract the reaction mixture with 50 ml of methylene chloride and 50 ml of water. Separate the organic phase, dry over magnesium sulfate, filter and evaporate to dryness in vacuo. Purify by preparative thin layer chromatography on 1000μ silica gel plates eluting with ethyl acetate.

Step C - 4-Phenyl-1,2,4-triazoline-3,5-dione Adduct of 22ξ-Mesyl-27-norcholest-6-ene-3-acetate Ethylene Ketal Dissolve 2.72 gm of the alcohol of Step B in 35 ml of dry pyridine and add 6.3 ml of methanesulfonyl chloride over a one hour period. Continue stirring for an additional 18 hours. Pour the reaction mixture into 200 ml of ice water slurry. Separate the precipitate by filtration and dry at 70° C over phosphorous pentoxide.

Step D - 3β-Hydroxy-27-norcholest-5,7-diene Ethylene Ketal

Dissolve 680 mg of crude mesylate from Step C in 35 ml of dry tetrahydrofuran. Add 680 mg of lithium aluminum hydride in portions with stirring at room temperature over a one hour period. Reflux the reaction mixture for 24 hours and cool to 0° to 10° C. Add 1 ml of ethyl acetate then 20 ml of water of destroy the excess lithium aluminum hydride. Extract with 100 ml of methylene chloride. Separate the organic phase, dry over magnesium sulfate, filter and evaporate the filtrate to dryness.

Step E - 3β-Hydroxy-27-norcholest-5,7-dien-25-one

Dissolve 80 mg of the ketal of Step D in 3 ml of acetic acid and 1 ml of water. Stir the mixture at room temperature for 18 hours. Extract the reaction mixture with two 20 ml portions of methylene chloride containing 5 ml of water. Separate the organic phase, dry over magnesium sulfate, filter and concentrate the filtrate to dryness. Purify by preparative thin layer chromotography on 1000 M silica gel plates eluting with 2% ethanol in ethyl acetate. Crystallize the product from ethyl acetate (mp 89°-91° C-not reduced on admixture with an authentic sample-Journal of Labelled Compounds IX, 339-341, 1973.

The subject matter which applicant regards as his invention is particularly pointed out and distinctly claimed as follows:

What is claimed is:

1. A process for preparing 3β-hydroxy-27-norcholest-5,7-dien-25-one of the formula:

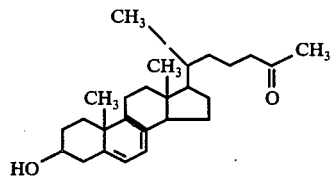

which comprises:
(a) ozonizing the 4-phenyl-1,2,4-triazoline-3,5-dione adduct of egosterol acetate of formula I at −70° to −80° C and reducing in situ the ozonide so formed to produce the 4-phenyl-1,2,4-triazoline-3,5-dione adduct of 3β-acetoxycholest-6-ene-hexanoraldehyde formula II;
(b) alkylating the aldehyde of formula D with 2-(1,3-dioxolane-2-methyl)ethyl bromide at −20° to −40° C to produce the 4-phenyl-1,2,4-triazoline-3,5-dione adduct of 22 ξ-hydroxy-27-norcholest-6-ene-3-acetate ethylene ketal of formula III;
(c) treating the alcohol of formula III with methylsulfonyl chloride to produce the 4-phenyl-1, 24,-triazoline-3-5-dione adduct of 22ξ-mesyl-27-norcholest-6-ene-3-acetate ethylene ketal of formula IV;
(d) reducing the mesylate of formula IV with lithium aluminum hydride at 0° to 10° C to produce 3β-hydroxy-27-norcholest-5,7-diene ethylene ketal of formula V; and
(e) treating the diene of formula V with aqueous acetic acid to produce the 3β-hydroxy-27-norcholest-5,7-dien-25-one of formula VI.

2. A compound of structural formula:

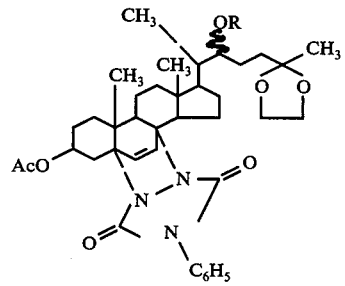

wherein R is a member selected from the group consisting of hydroxy and mesyl.

* * * * *